(12) United States Patent
Slager et al.

(10) Patent No.: US 8,709,827 B2
(45) Date of Patent: Apr. 29, 2014

(54) POLYPEPTIDE MICROPARTICLES

(75) Inventors: Joram Slager, St. Louis Park, MN (US); John V. Wall, Woodbury, MN (US)

(73) Assignee: SurModics, Inc., Eden Prairie, MN (US)

( * ) Notice: Subject to any disclaimer, the term of this patent is extended or adjusted under 35 U.S.C. 154(b) by 1241 days.

(21) Appl. No.: 12/215,504

(22) Filed: Jun. 27, 2008

(65) Prior Publication Data

US 2009/0028956 A1   Jan. 29, 2009

Related U.S. Application Data

(60) Provisional application No. 60/937,492, filed on Jun. 28, 2007.

(51) Int. Cl.
*G01N 33/558* (2006.01)
*C07K 16/00* (2006.01)
*A61K 31/28* (2006.01)

(52) U.S. Cl.
USPC ......... 436/514; 530/387.1; 514/492; 514/495

(58) Field of Classification Search
None
See application file for complete search history.

(56) References Cited

U.S. PATENT DOCUMENTS

| | | | |
|---|---|---|---|
| 5,635,216 A | 6/1997 | Thompson | |
| 5,980,948 A | 11/1999 | Goedemoed et al. | |
| 6,020,004 A | 2/2000 | Shah | |
| 6,165,508 A * | 12/2000 | Tracy et al. | 424/487 |
| 6,268,053 B1 | 7/2001 | Woiszwillo et al. | |
| 6,331,317 B1 | 12/2001 | Lyons et al. | |
| 6,723,429 B2 | 4/2004 | Bengs et al. | |
| 6,773,928 B1 * | 8/2004 | Yin et al. | 436/518 |
| 6,862,890 B2 | 3/2005 | Williams, III et al. | |
| 7,105,181 B2 | 9/2006 | Gustavsson et al. | |
| 7,638,344 B2 * | 12/2009 | Slager et al. | 436/514 |
| 2002/0009457 A1 * | 1/2002 | Bowersock et al. | 424/184.1 |
| 2004/0219224 A1 * | 11/2004 | Yakovlevsky et al. | 424/499 |
| 2005/0123596 A1 * | 6/2005 | Kohane et al. | 424/450 |
| 2005/0255142 A1 * | 11/2005 | Chudzik et al. | 424/426 |
| 2008/0038354 A1 | 2/2008 | Slager et al. | |
| 2009/0022805 A1 * | 1/2009 | Slager et al. | 424/486 |
| 2011/0319473 A1 * | 12/2011 | McGonigle et al. | 514/44 A |

FOREIGN PATENT DOCUMENTS

| | | |
|---|---|---|
| EP | 1 555 278 | 1/2004 |
| WO | 91/16038 | 10/1991 |
| WO | 2006/088473 | 8/2006 |

OTHER PUBLICATIONS

PCT International Search Report for International Application No. PCT/US2008/0007999, mailed on May 11, 2008.
Ruth et al.(2000) α-L-Iduronidase forms semi-crystalline spherulites with amyloid-like properties. Acta Crystallographica, 56: 524-528.
Johnston, et al.(2007) Stable Protein Nanoparticles by Rapid Freezing for Enhanced Delivery. Department of Chemical Engineering, The University of Texas at Austin.
Stura E.A., et al.(1993) Crystallization of Antibodies and Antibody-Antigen Complexes. Immunomethods, 3: 164-179.
U.S. Appl. No. 60/806,030, Jun. 28, 2006, Slager, et al.

* cited by examiner

*Primary Examiner* — Maury Audet
(74) *Attorney, Agent, or Firm* — Kagan Binder, PLLC

(57) ABSTRACT

The invention provides polypeptide microparticles and methods for the preparation thereof using a nucleating agent.

18 Claims, 3 Drawing Sheets

POLYPEPTIDE MICROPARTICLES

CROSS-REFERENCE TO RELATED APPLICATION

This application claims the benefit of U.S. Provisional Patent Application Ser. No. 60/937,492, filed Jun. 28, 2007, entitled POLYPEPTIDE MICROPARTICLES, the disclosure of which is incorporated herein by reference.

FIELD OF THE INVENTION

The present invention relates to a polypeptide microparticles and methods for their formation. The present invention also relates to methods and systems using polypeptide microparticles used as a therapeutic agent.

BACKGROUND

Therapeutic agents can be introduced into a subject by several different routes. Most commonly, therapeutic agents are orally administered because it is a convenient, safe, and cost effective way to making the agent systemically available to the body. However, in many cases, oral administration is not preferred. For example, certain therapeutic agents are not stable in, or taken up into the body by the digestive tract. Therapeutic agents such as proteins, polypeptides, or oligopeptides (collectively referred to herein as "polypeptides") are typically not orally administered.

Therapeutic polypeptides are typically administered by routes that avoid conditions that destroy the polypeptide, such as would occur with proteolysis in portions of the digestive tract. Commonly used injection routes for polypeptides include subcutaneous, intramuscular, and intravenous injections. Frequent injections are often necessary due to short plasma half-lives of polypeptides. In some cases, mucosal administration of polypeptides can be performed using methods that place the polypeptide in contact with membranes lining the urogenital or and respiratory tracts.

Many current therapeutic preparations of polypeptide therapeutics are liquid formulations (for example, liquid formulations of insulin), which are injected into a subject to provide a therapeutic effect. However, many of these injectable compositions provide a therapeutic response over a limited period of time.

Solid formulations of polypeptides have been prepared in attempt to lengthen the therapeutic window for polypeptide. One approach is to crush or grind lyophilized polypeptides into small particulates, which can be administered to a patient. This approach is less than desirable as it results in the formation of particulates substantially heterogenous in size and shapes. This approach can also be detrimental to the activity of the polypeptide if aggressive techniques are used to create the particulates.

Another approach for delivering polypeptides to a subject is to use polymer microparticles that are associated with polypeptides. Microparticles refer to those particles having a diameter of less than 1 mm, and are more typically found as having a diameter of less than 0.1 mm (100 µm). Most microparticles are spherical in shape (i.e., microspheres), although microparticles may be observed having other non-spherical shapes. Spray drying, phase separation, solvent evaporation, and emulsification are common techniques used to make microparticles, which are typically formed from synthetic or natural polymers. For purposes of drug delivery, microparticles made using these techniques can have desirable properties, such as size and uniformity. However, many microparticle preparations have low polypeptide content due the presence of a larger content of excipient polymer in the microparticle. This can significantly limit the amount of polypeptide that can become available to a subject upon administration of the microparticles.

The preparation of microparticles having a high polypeptide content, such as those composed predominantly or entirely of polypeptides, can be very challenging. Standard techniques may lead to polypeptide microparticle preparations that are highly amorphous and that do not resemble microparticles, substantially aggregated, non-dissolvable peptide particles, or highly cracked or fractured protein particles. Some techniques may not even form particles.

Another challenge involves the preparation of a batch (e.g., a "set") of polypeptide microparticles that have low size polydispersity. A set of polypeptide microparticles polypeptide having a low size polydispersity tends to have fewer polypeptides microparticles in the set of a size that considerably deviate in size from the mean microparticle size of the set. Previous techniques, however, often provide microparticle sets with higher size dispersity, and there is no particularly good technique for removing microparticles from the set that are of sizes that substantially deviate from the mean size of the set. In applications of the present invention, it has been found desirable to produce sets of microparticles having low size polydispersity.

The present invention addresses challenges in the art of polypeptide microparticle preparation and provides improvements for the preparation of microparticles having desirable particle shape, particle morphology, polypeptide release and activity, and particle size dispersity.

The present invention also addresses challenges in the art of localized or site-specific delivery of bioactive agents, and allows for improvements in bioactive agent release rates and bioactive agent activity, which can generally provide improved treatment for subjects with particular medical conditions.

SUMMARY

The present invention is directed to polypeptide microparticles and particular methods for the preparation of these microparticles. The invention is also directed to the use of polypeptide microparticles for the treatment of a medical condition in a subject, in which polypeptides are released from the microparticles and provide a therapeutic effect to a subject. For example, the polypeptide microparticles can be used in association with a drug delivery system that is implanted or formed at a target location in the body.

In many aspects, the polypeptide microparticles can be placed within the body where they dissolve and polypeptide is released, providing a therapeutic effect to a subject. The microparticles can be introduced into the body alone, or in combination with another component that can modulate release of the polypeptides from the polypeptide microparticles. The polypeptide microparticles can be used in therapies so the polypeptide exerts a site-specific effect, or alternatively, a more general systemic therapeutic throughout the body.

The methods of the invention provide polypeptide microparticles having a high polypeptide content, being formed predominantly or entirely of polypeptide. This can be important in many therapeutic methods, as the amount of polypeptide that is available to a subject following administration of the microparticles can be maximized. This is also advantageous for applications involving the site-specific delivery of polypeptides, or the delivery of polypeptides to a limited access region in the body. As another advantage, the amount of secondary materials present in, and capable of being released from the microparticle can be minimized, which can be desirable for patient safety.

As another advantage, the microparticles can be formed with little or no loss of polypeptide bioactivity.

The methods of the invention also allow formation of a set of microparticles having a population of a lower size polydispersity (expressed herein as a low "degree of monodispersity" value (DM)). In other words, there is not considerable size variation among the polypeptide microparticles of a microparticle set formed according to the methods of the invention. This is advantageous in processes wherein particular delivery techniques or equipment are used (such as when the microparticles are delivered via small diameter conduits), or when the microparticles are immobilized in a thin biocompatible coating on the surface of a medical device.

A degree of monodispersity that is low is also advantageous for releasing polypeptide in a more controlled manner after the microparticles have been introduced in the body. For example, a polypeptide microparticle set with a low degree of monodispersity can be used to prepare a polypeptide microparticle-containing coating, which has uniform coating properties, and which can release polypeptide at a more predictable rate in the body.

In one aspect, a set of polypeptide microparticles is prepared by a method that includes a step of coalescing polypeptides with a nucleating agent to form polypeptide nuclei, which is performed in a liquid composition. Next, phase separation reagent (such as an amphiphilic polymer) is mixed with the composition to further coalesce polypeptide around the nuclei. Next, the composition is cooled. Following this, all or a portion of the phase separation reagent is removed from the composition, which provides the set of polypeptide microparticles having a high polypeptide content.

Various nucleating agents can be used in a nucleating amount to form polypeptide nuclei. In some aspects of the invention, the nucleating agent comprises a divalent cation (for example, such as calcium). In some aspects of the invention, the nucleating agent comprises a noble metal colloid (for example, such as a colloidal gold). In some aspects of the invention, the nucleating agent comprises a polyplex (e.g., a complex of a polynucleotide and a polycation), or a thermoplastic nanosphere, such as a polystyrene nanosphere.

The method of the invention can be performed for the preparation of microparticles formed of antibodies or antibody fragments, such as Fab or Fab'2 fragments. In this regard, the present method is particularly advantageous, because the formation of particulates of antibody fragments can be very difficult.

In one aspect of the invention, the step of mixing the phase separation agent is carried out above room temperature. In this step, the composition containing polypeptide nuclei can be provided above room temperature, above 37° C., and most preferably at about 50° C. or greater, and then mixed with the phase separation agent at or about the same temperature. Use of these higher temperatures in the mixing step facilitates the formation of a set of protein microparticles with a remarkably low size polydispersity. In preferred modes of practice, the mixture is briefly mixed and then cooled.

The invention also provides methods for preparing microparticle sets, wherein the microparticles of the set have a mean diameter that is within a desired discrete size range, wherein the mean sizes are less than 10 μm. Following the step of mixing, the polypeptide microparticle mixture is cooled to a temperature of about −20° C. or less, which represents another inventive aspect of the invention. Accordingly, microparticles having an average size in the range of about 0.3 μm to about 10.0 μm are generally prepared by cooling the microparticles to a temperature of about −20° C. or less after mixing with the phase separation agent.

For the preparation of a set of microparticles having a diameter (mean) in the range of about 1 μm to about 2 μm, the microparticles are immediately cooled to a temperature of about −40° C. or less, such as about −80° C.

For the preparation of a set of microparticles having a diameter (mean) in the range of about 3 μm to about 4 μm, the microparticles are immediately cooled to a temperature in the range of below 0° C. to −40° C., such as about −20° C.

For the preparation of a set of microparticles having a diameter (mean) in the range of about 5 μm to about 6 μm, the particles are more slowly cooled to a temperature of −20° C. (for example, the cooling can include a gradual cooling over a period of time, or a series of intermediate cooling steps).

The structure of the resultant polypeptide microparticle comprises a center of a nucleus or nuclei. The nucleus or nuclei includes the nucleating agent and polypeptide. The nucleus or nuclei are further surrounded by polypeptide. The microparticle can also have desirable characteristics, such as a generally spherical shape, and little or no surface irregularities (e.g., cracks). In some aspects, the polypeptide microparticle has a diameter of about 10 μm or less, and in more specific aspects, in the range of about 0.3 μm to about 10 μm.

The method of the invention can also provide a polypeptide microparticle set with a low degree of monodispersity value. This can be desirable for various end uses for the microparticles, and can provide subsequent improvements in polypeptide release rates, coating formation, and/or microparticle delivery. In some aspects, the set comprises a plurality of polypeptide microparticles, wherein polypeptide is the predominant component in the individual polypeptide microparticles of the set and polypeptide microparticles comprise a nucleus or nuclei comprising a nucleating agent, and wherein the set has a degree of monodispersity of 5 or less. In more specific aspects, the polypeptide microparticle set has a degree of monodispersity in the range of 0.5 to 5.

The polypeptide microparticles can be used in drug delivery methods wherein the polypeptide is a therapeutic agent. The polypeptide microparticles can be introduced into a subject by injection, or can be used in a delivery system that modulates release of the polypeptide. In some aspects, the polypeptide microparticles of the present invention are used to deliver polypeptide at an intravascular location, or at a limited access region in the body, such as the eye.

The polypeptide microparticles can also be used in conjunction with a drug delivery device. The polypeptide microparticles can be associated with the device, in a manner that they are releasable from, immobilized on or within the device, or both.

The polypeptide microparticles can also be used in conjunction with a polymer system that modulates release of the polypeptide. The polymer system can be biostable or biodegradable.

In some cases the polypeptide microparticles are immobilized in a polymeric matrix that is associated with an implantable medical device (such as in a coating on a surface of the device). The microparticles can also be immobilized in an in-situ formed body of polymeric material (such as a crosslinked hydrogel).

DETAILED DESCRIPTION

Figure 1A:
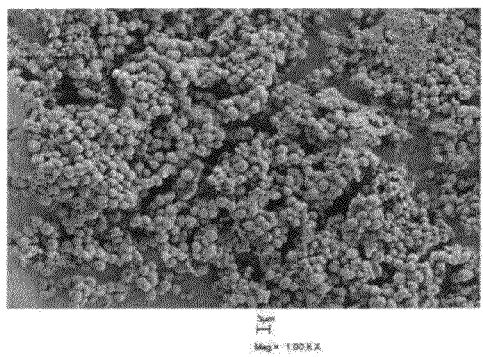
FIGS. 1a and 1b are scanning electron microscope (SEM) images of $CaCl_2$-nucleated Fab microparticles.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present invention provides polypeptide microparticles having a high polypeptide content, and methods for forming these particles. The process of the invention provides a "set" of microparticles, which refers to all of the microparticles that are included in a microparticle sample produced according to the methods of the invention. The methods of the invention also provide polypeptide microparticle sets with low degree of monodispersity values.

The polypeptide microparticles can be placed in a subject, alone or in combination with a delivery article, in a manner so the polypeptides become therapeutically available to the subject. In some more specific delivery approaches, the polypeptide microparticles can be associated with an implantable delivery article for the site-specific release of polypeptides.

As used herein, a polypeptide refers to an oligomer or polymer including two or more amino acid residues, and is intended to encompass compounds referred to in the art as proteins, polypeptides, oligopeptides, peptides, and the like. More, specific classes of peptides include enzymatic polypeptides (enzymes), antibodies, antibody fragments, neuropeptides, and peptide hormones. The twenty, common, naturally-occurring amino acids residues and their respective one-letter symbols are as follows: A (alanine); R (arginine); N (asparagine); D (aspartic acid); C (cysteine); Q (glutamine); E (glutamic acid); G (glycine); H (histidine); I (isoleucine); L (leucine); K (lysine); M (methionine); F (phenylalanine); P (proline); S (serine); T (threonine); W (tryptophan); Y (tyrosine); and V (valine).

The polypeptides can also include one or more rare and/or non-natural. Naturally occurring, rare amino acids include selenocysteine (Sec) and pyrrolysine (Pyl). Non-natural amino acids are typically organic compounds having a similar structure and reactivity to that of naturally-occurring amino acid counterpart. Non-natural amino acids include, for example, cyclic amino acid analogs, amino alcohols, D-amino acids, propargylglycine derivatives, beta amino acids, gamma amino acids, 2-amino-4-cyanobutyric acid derivatives, and Weinreb amides of α-amino acids. Incorporation of such amino acids into a polypeptide may serve to increase the stability, reactivity and/or solubility of the polypeptide Polypeptides of the invention can also include those that are modified with, or conjugated to, another biomolecule or biocompatible compound. For example, the polypeptide can be a peptide-nucleic acid (PNA) conjugate, polysaccharide-peptide conjugates (e.g., glyosylated polypeptides; glycoproteins), a poly(ethyleneglycol)-polypeptide conjugate (PEGylated polypeptides).

In some modes of practice, the polypeptide microparticles are prepared from polypeptides having a molecular weight of about 10,000 Da or greater, or about 20,000 Da or greater; more specifically in the range of about 10,000 Da to about 100,000 Da, or in the range of about 25,000 Da to about 75,000 Da.

One class of polypeptides that can be formed into the microparticles of the invention includes antibodies and antibody fragments. Antibodies (immunoglobulins) are large glycoproteins (typically of about 100,000 Da or greater) containing antigen binding regions and have an overall "Y" shape. The polypeptides of the microparticle can be glycosylated, since antibody polysaccharide chains are typically attached to amino acid residues by N-linked glycosylation and occasionally by O-linked glycosylation.

The polypeptides can also include a disulfide bond; an antibody consists of two identical heavy chains and two identical light chains that are connected by disulfide bonds. Each heavy chain has two regions, known as the constant and variable regions. The polypeptides can also include an immunoglobulin domain; the variable domain of any heavy chain is composed of a single immunoglobulin domain which is about 110 amino acids long. A light chain has two successive domains: one constant domain and one variable domain. The polyp eptide can also include a peptide sequence capable of affinity interaction with a ligand; the variable regions of the heavy and light chains provide antigen/epitope binding specificity.

This portion of the antibody region is called the Fab (fragment, antigen binding) region of the antibody and is composed of one constant and one variable domain from each heavy and light chain of the antibody. The paratope is shaped at the amino terminal end of the antibody monomer by the variable domains from the heavy and light chains.

Antibody light and heavy chains are composed of structural domains called immunoglobulin (Ig) domains. These domains contain about 70-110 amino acids and are classified into different categories (for example, variable or IgV, and constant or IgC) according to their size and function. They possess a characteristic immunoglobulin fold in which two beta sheets create a "sandwich" shape, held together by interactions between conserved cysteines and other charged amino acids.

A variety of antibody and antibody fragments are commercially available, obtainable from deposited samples, or can be prepared by techniques known in the art.

Monoclonal antibodies (mAbs) can be obtained by any technique that provides for the production of antibody molecules by continuous cell lines in culture. These include, for example, the hybridoma technique (Kohler and Milstein, Nature, 256:495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD and any subclass thereof. Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

Examples of antibodies and antibody fragments that can be used to prepare the microparticles of the present invention include, but are not limited to, therapeutic antibodies include trastuzumab (Herceptin™), a humanized anti-HER2 monoclonal antibody (moAb); alemtuzumab (Campath™), a humanized anti-CD52 moAb; gemtuzumab (Mylotarg™), a humanized anti-CD33 moAb; rituximab (Rituxan™), a chimeric anti-CD20 moAb (Zevalin™), a murine moAb conjugated to a beta-emitting radioisotope; tositumomab (Bexxamm™), a murine anti-CD20 moAb; edrecolomab (Panorex™), a murine anti-epithelial cell adhesion molecule moAb; cetuximab (Erbitux™), a chimeric anti-EGFR moAb; bevacizumab (Avastin™), a humanized anti-VEGF moAb, Ranibizumab (Lucentis™), an anti-vascular endothelial growth factor moAb fragment, satumomab (OncoScint™) an anti-pancarcinoma antigen (Tag-72) moAb, pertuzumab (Omnitarg™) an anti-HER2 moAb, and daclizumab (Zenapax™) an anti IL-2 receptor moAb.

The polypeptide can also be selected from cell response modifiers. Cell response modifiers include chemotactic factors such as platelet-derived growth factor (PDGF), human pigment-epithelium derived growth factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The polypeptide can also be selected from therapeutic enzymes, such as proteases, phospholipases, lipases, glycosidases, cholesterol esterases, and nucleases.

Specific examples include recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase.

The polypeptides can be subjected to any purification or enrichment process prior to being used to form the polypeptide microparticles of the invention. Exemplary purification or enrichment techniques include one or more affinity, hydrophobic, size exclusion, centrifugal, and liquid chromatographies (such as HPLC).

The first step in the process of preparing the polypeptide microparticles involves the formation of polypeptide nuclei by coalescing polypeptide with nucleating agent. This can be achieved by first preparing a liquid composition that includes the polypeptide, and then adding nucleating agent to the liquid composition in an amount sufficient to promote nuclei formation. The nucleating agent is used in a "nucleating amount," which is an amount of nucleating agent that causes formation of polypeptide nuclei during the nucleation step. Examples of suitable amounts of nucleating agents used in the process of the invention are described herein.

The nucleation step can be performed in any suitable receptacle, formed of material that does not significantly interfere with the nucleation process. The receptacle can be formed of plastic, glass, or metal, the inner surfaces of which can optionally be treated to minimize or eliminate any non-specific adsorption of the polypeptide or nucleating agent to the surfaces. Exemplary thermoplastics receptacles are fabricated from polypropylene, polystyrene, poly(tetrafluoroethylene) (PTFE), and perfluoroalkoxy (PFA) polymers, such as Teflon™ and Neoflon™.

Generally, in many modes of practice, the liquid composition is an aqueous solution of polypeptide. The preparation of this solution may involve, for example, the solubilization of a lyophilized polypeptide, or the dilution of a concentrated solution of polypeptide with an aqueous solution. The polypeptide solution can be prepared as an aqueous buffered solution. Exemplary buffers include sodium phosphate (e.g., phosphate-buffered saline), and 2(N-morpholino) ethanesulfonic acid (MES), which can be used at concentrations of about 5 mM in the polypeptide solution.

The pH of the polypeptide solution can be prepared to facilitate polypeptide nuclei formation. In some cases, the pH of the polypeptide solution can be prepared to be at about or near the pKa of a polypeptide that is formed into the microparticles. In many modes of practice, the pH of the polypeptide solution is in the range of about pH 5-7. pH can be controlled by the addition of commonly used acids or bases to the aqueous solution.

The polypeptide is dissolved in solution at a concentration sufficient for the formation of polypeptide nuclei when a nucleating agent is added to the polypeptide solution. In many preparations, the concentration of polypeptide in solution is generally at about 10 mg/mL or greater. However if a chosen polypeptide is easily coalesced with the nucleating agent to form nuclei, lower concentrations of polypeptide may be used. In some specific modes of practice, the polypeptide is an antibody or Fab fragment, which is in solution at a concentration in the range of about 10 mg/mL to about 50 mg/mL, and more specifically in the range of 15 mg/mL to about 20 mg/mL.

The liquid composition is prepared so that the polypeptide microparticles formed are predominantly of polypeptide. A polypeptide microparticle formed "predominantly" of polypeptide is a microparticle that, by weight, contains more polypeptide than one, or more than one, other components (compared individually) in the polypeptide microparticle. To illustrate this, the polypeptide microparticles of the invention include, in the least, a polypeptide (e.g., component A) and a nucleating agent (e.g., component B), wherein the polypeptide is present in a greater amount by weight than the nucleating agent in the polypeptide microparticle. Optionally, the polypeptide microparticle may include other components (for example, components C, D, or E, etc., or combinations thereof). However, if optional components such as C, D, or E, etc., are included each of these optional components individually would be present, by weight, in an amount less than that of the polypeptide.

Preferably, the formed polypeptide microparticle comprises an amount of polypeptide, by weight, of about 90% or greater, such as in the range of about 90% to about 99.99%, of about 95% or greater, such as in the range of about 95% to about 99.99%, of about 97.5% or greater, such as in the range of about 97.5% to about 99.99%, of about 99% or greater, such as in the range of about 99% to about 99.99%, of about 99.5% or greater, such as in the range of about 99.5% to about 99.99%.

Preferably, the polypeptide microparticle is formed predominantly of a single type of antibody, or antibody fragment. Preferably, the antibody, or antibody fragment, is present in the polypeptide microparticle in an amount within a range as described above.

Preparation of the polypeptide solution can be carried out at a temperature suitable for the polypeptide to dissolve. In some cases the polypeptide is preferably dissolved in solution at a lower temperature, such as below about 20° C., or below about 10° C.

The formation of polypeptide microparticles includes a nucleation step that brings polypeptide molecules in close enough proximity to allow formation of a nucleus. Formation of the polypeptide nucleus can be initiated by the addition of nucleating agent to the polypeptide solution. Generally, the nucleating agent is prepared in a solution, which is miscible with the polypeptide solution, and then the nucleating agent solution is added to the polypeptide solution. The nucleus that is formed can be capable of fully or partially dissolving in an aqueous environment, such as body fluids.

In one mode of practice, the nucleation step provides a polypeptide nucleus formed by electrostatic interactions between the divalent cations and the polyanionic charges available from a polypeptide, such as a large protein molecule like IgG and related fragments. The resulting polypeptide microparticle with the divalent cation formed polypeptide nucleus or nuclei can be soluble, and the amount of divalent cation used for nucleus formation can be adjusted to provide for elution control by varying the amount of the divalent cation during the nucleation step.

In some aspects, the nucleating agent comprises a divalent cation. Various divalent cations are contemplated nucleating agents. These include calcium, zinc, magnesium, manganese, iron, copper, cobalt and nickel. More specifically, the divalent cation can be a Group IIA metal, such as calcium or magnesium. A solution containing the divalent cation is typically provided to the solution from a salt form (divalent cation/anion). Exemplary salts of divalent cations are those formed from anions such as chloride, citrate, ascorbate, borate, phosphate, bicarbonate, sulfate, thiosulfate, bisulfate, sodium bisulfate, ammonium sulfate. Exemplary salts that can be used to form the microparticle nuclei are selected from calcium salts such as $CaCl_2$, $CaSO_4$, $Ca(NO_3)_2$ and $CaCO_3$. Other exemplary salts are selected from magnesium salts such as $MgCl_2$ or $MgSO_4$. Mixtures of divalent cations can also be used as the nucleating agent.

In some modes of practice, the divalent cation is prepared in a solution at a high concentration, and then the highly concentrated solution of divalent cation is added to the polypeptide solution. The highly concentrated solution of divalent cation may be, about 250 mM or greater, about 500 mM or greater, or even about 1 M or greater. Using a highly concentrated solution, a smaller volume of nucleating agent solution can be added to the polypeptide solution in the nucleation step.

The divalent cation is added at a concentration to promote formation of the polypeptide nucleus. In many modes of practice, the divalent cation is added to the polypeptide solution so the final concentration of the cation is about 1 mM or greater. However, some polypeptides may more easily coalesce and polypeptide nuclei can be formed at concentrations of cation of less than 1 mM. One may choose the appropriate amount of divalent cation to provide a solution of nucleated polypeptides in the nucleation step of the process. Generally, the nucleation step will result in the formation of polypeptide nuclei, with also an amount of free polypeptide left in solution. The amount of free polypeptide left in solution is used in the step further coalescing the free polypeptide around the polypeptide nuclei with the polymeric material. In this regard, the use of amounts of divalent cation that would otherwise cause all of the polypeptide to be precipitated out of solution are generally avoided.

In some preferred modes of practice the divalent cation is added to a final concentration of about 1 mM to about 10 mM, about 1.5 mM to about 7.5 mM, about 1.75 mM to about 5 mM, about 2 mM to about 3.5 mM, or about 2.5 mM.

The amount of peptide and nucleating agent in the nucleation step can also be expressed as the molar ratio of the polypeptide to the nucleating agent. For example, for a polypeptide having an average MW of about 40 kDa (such as a Fab fragment) the ratio of the Fab fragment to the cation is in the range of about 1.25:1 to about 1:40, and more preferably in the range of about 0.5:1 to about 1:10. (10 mg/mL Fab is ~0.25 mM, 50 mg/mL Fab is ~1.25 mM).

The divalent cation can be added to the polypeptide solution and the solution agitated to rapidly mix the nucleating agent with the polypeptide. The mixed solution can be incubated for a period of time to allow for nuclei formation. Depending on the factors, such as the type and concentration of the polypeptide and nucleating agent, the nucleation period can be rather short (such as about 10 min or less) or may be carried out for many hours. In one mode of practice, nucleation of a polypeptide solution containing a divalent cation is carried out for a period of about 1 hour. Also, in some desired modes of practice, the mixture with the divalent cation is incubated at a temperature below room temperature, and preferably between about 0° C. and 10° C.

Depending on the nucleating agent used, formation of polypeptide nuclei can be determined visually, or by other methods, such as by spectrometry. For example, the solution may be clear at the onset of the nucleation step, and then turn very slightly cloudy upon formation of polypeptide nuclei. However, in some cases, polypeptide nuclei may be formed even though there is not a distinct visual difference between the un-nucleated peptide solution, and the solution where nucleated polypeptide has formed. Therefore, in some modes of practice, it can be desirable to monitor formation of polypeptide nuclei spectrophotometrically. Spectrophotometric measurements may be useful for determining the optimal conditions for nucleation.

In some aspects, the nucleating agent comprises a noble metal colloid. The term "noble metal colloid" generally refers to nanoparticulates formed of one or more noble metals. Noble metals include those such as gold, silver, tantalum, platinum, palladium and rhodium. A solution/suspension of monodisperse spherical gold nanoparticles (colloidal gold) can be obtained commercially (from, for example, Sigma-Aldrich, Milwaukee, Wis.) or prepared by the reduction of gold ions, for example, chloroauric acid, with a reducing agent, such as citrate, (see for example, G. Frens, Nature Phys. Sci., 241: 20-22 (1973)). The particle diameter of the colloidal gold particles can be altered using particular ratios of reducing agent to chloroauric acid. Average sizes (diameter) of these colloidal gold nanoparticles typically range from about 1 nm to about 50 nm, which can be used to form polypeptide nuclei in the nucleating step. Typically, commercially available preparations are provided as a percent weight/volume (e.g., 0.01% w/v colloidal gold).

In some desired modes of practice, the noble metal colloid has an average size of about 1 nm to about 20 nm, or about 1 nm to about 10 nm, and is used to prepare polypeptide nuclei.

For example, polypeptide nuclei can be prepared using colloidal gold having an average size of about 5 nm.

In many modes of practice, the noble metal colloid is added to the polypeptide solution so the final concentration of the noble metal colloid is about 1 µg/mL or greater. However, some polypeptides may more easily coalesce in the presence of the noble metal colloid to form polypeptide nuclei, and the noble metal colloid may used formed at concentrations of cation of less than 1 µg/mL. One may choose the appropriate amount of noble metal colloid to provide a solution of nucleated polypeptides in the nucleation step of the process.

In some preferred modes of practice the noble metal colloid is added to a final concentration of about 1 µg/mL to about 10 µg/mL, about 1.5 µg/mL to about 7.5 µg/mL, about 1.75 µg/mL to about 5 µg/mL, about 2 µg/mL to about 3.5 µg/mL, or about 2.5 µg/mL.

In some modes of practice, the nucleating step is carried out using a weight ratio of a noble metal colloid, such as colloidal gold, to polypeptide, such as Fab fragment, in the range of about 1:100 to 1:10,000, more specifically in the range of about 1:1,000 to 1:10,000, or about 1:8,000.

The noble metal colloid can be added to the polypeptide solution and the solution agitated to rapidly mix the noble metal colloid with the polypeptide.

Again, depending on the factors, such as the type and concentration of the polypeptide and noble metal colloid, the nucleation period can be rather short (such as about 10 min or less) or may be carried out for many hours. In one mode of practice, nucleation of a polypeptide solution containing a noble metal colloid is carried out for a period of between about 30 minutes and 1 hour. Also, in some desired modes of practice, in the nucleating step using the noble metal colloid, the mixture is incubated at a temperature above room temperature, and preferably between about 30° C. and 70° C. In one exemplary mode of practice, the mixture with the noble metal colloid is incubated at about 50° C.

In other modes of practice, polypeptide nuclei can be formed using a nucleating agent that comprises a polyplex. Polyplexes are typically formed by polycationic carrier molecules that bind and condense nucleic acids and form complex structures with an excess positive charge. The nucleating agent used to form the polypeptide microparticles can be a polyplex that includes at least the polycationic carrier molecule and a nucleic acid. Other components can be included in the polyplex, such as secondary polymers or nucleic acids. Commercially available polycationic carrier molecules and nucleic acids, such as, polyethylenimine (PEI) and herring DNA are suitable components for the formation of a nucleating agent that is a polyplex.

Therefore, in another mode of practice a nucleating agent that is a polyplex is obtained or prepared, and then added to a polypeptide solution to form polypeptide nuclei. For example, in one mode of practice, a polyplex is prepared by combining PEI and DNA. As a general matter, the PEI reagent provides a particular number of primary amino groups ("N") per weight unit, and the DNA provides a particular number of charged phosphate groups ("P") per weight unit. The PEI and DNA can be combined to provide a desired N:P ratio. In some aspects the N:P ratio is in the range of about 10:1 to about 25:1. The polyplex can be formed in the presence of an excipient, such as sucrose.

Nucleation can be performed by mixing a polyplex composition with a polypeptide solution for a period of time. For example, the final concentration of the polyplex in the mixed composition is in the range of about 0.01% (w/v) to about 1% (w/v).

Again, depending on the factors, such as the type and concentration of the polypeptide and polyplex, the nucleation period can be rather short (such as about 5 min or less) or may be carried out for many hours. In one mode of practice, nucleation of a polypeptide composition containing a polyplex is carried out for a period of between about 5 minutes to about 1 hour. Also, in some desired modes of practice, in the nucleating step using the polyplex, the mixture is incubated at a temperature above room temperature, and preferably between about 30° C. and 70° C. In one exemplary mode of practice, the composition is incubated at about 50° C.

In other modes of practice, polypeptide nuclei can be formed using a nucleating agent that is a thermoplastic nanosphere. Exemplary thermoplastic nanospheres can be prepared from aromatic thermoplastic polymers such as polystyrene and are commercially available (from, for example, Bangs Laboratories, Fishers, Ind.). The thermoplastic polymers can promote polypeptide nucleation by adsorption of the protein to the nanoparticle surface via ionic interactions. Exemplary thermoplastic nanospheres have sizes of about 100 nm or less, such as about 40 nm or less.

The nucleation step provides a colloidal liquid composition of polypeptide nuclei. The polypeptide nuclei have a very small size that are generally between the size of the starting materials (i.e., the nucleating agent or the polypeptide) and the size of the formed polypeptide microparticle. For example, these polypeptide nuclei may have sizes of greater than 5 nm.

Furthermore, in the nucleating step, both the nucleating agent and polypeptide are consumed in the nucleation step, which results in lower concentrations of free nucleating agent and polypeptide after the nucleation step. However, generally, in the nucleation step, the nucleating agent is substantially or entirely consumed (i.e., formed into polypeptide nuclei), while there is an amount of polypeptide remains "free" in solution (i.e., not formed into polypeptide nuclei).

Optionally, after the step of nucleation, additional polypeptide can be added to the liquid composition that includes the polypeptide nuclei. That is, if it is determined that the additional polypeptide should be added to facilitate subsequent steps of polypeptide microparticle formation, polypeptide can be added to the nucleated solution to increase the concentration of free polypeptide.

A subsequent step in the inventive process includes mixing the liquid composition that contains polypeptide nuclei with a phase separation agent. In this step, a phase separation reagent is added to the liquid composition including polypeptide nuclei and free polypeptide.

The phase separation reagent is a compound capable of being dissolved in both aqueous and organic solvents, and that can promote formation of the polypeptide microparticles. More particularly, the phase separation reagent is a compound capable of being dissolved in a solvent such as chloroform or dichloromethane, as well as in an aqueous solvent, and which can be separated from the polypeptide microparticles after they are formed. The phase separation agent can be an amphiphilic compound.

The amphiphilic compound can be selected from polymeric and non-polymeric amphiphilic materials. In some aspects of the invention, the amphiphilic compound is an amphiphilic polymer.

Exemplary amphiphilic polymers and compounds include poly(ethyleneglycol) (PEG) and PEG copolymers, tetraethylene glycol, triethylene glycol, trimethylolpropane ethoxylate, and pentaeerythritol ethoxylate, polyvinylpyrrolidone (PVP) and PVP copolymers, dextran, Pluronic™, polyacrylic acid, polyacrylamide, polyvinyl pyridine, polylycine, polyarginine, PEG sulfonates, fatty quaternary amines, fatty sulfonates, fatty acids, dextran, dextrin, and cyclodextrin. The amphiphilic polymer can also be copolymers of hydrophilic and hydrophobic polymeric blocks.

The amphiphilic compound can be added to the liquid composition having the nucleated polypeptides. In some aspects, a concentrated solution of an amphiphilic reagent (such as an amphiphilic polymer) is prepared and then added to the liquid composition having the nucleated polypeptides. In many modes of practice, the amphiphilic reagent is added to the liquid composition having the nucleated polypeptides so the final concentration of the amphiphilic reagent is about 1% (w/v) or greater. In more preferred aspects the final concentration of the amphiphilic reagent is in the range of about 2.5% (w/v) to about 12.5% (w/v), or more specifically about 5% (w/v) to about 10% (w/v). For example, an amphiphilic reagent such as PEG is used in the amount of about 7.5%.

In one desired mode of practice, prior to mixing, the liquid composition including polypeptide nuclei and the amphiphilic reagent are (individually) heated to a temperature above room temperature and then combined with good mixing at this elevated temperature. It has been discovered that using an elevated temperature is beneficial for microparticle formation as it facilitates the formation of a set of polypeptide microparticles with a low degree of monodispersity value.

For example, prior to mixing, the liquid composition including polypeptide nuclei and the amphiphilic reagent are individually heated to a temperature greater than room temperature, such as greater than 30° C., 35° C., 40° C., 45° C., or about 50° C. or greater, such as in the range of about 30° C. to about 90° C., from about 35° C. to about 85° C., from about 40° C. to about 80° C., from about 45° C. to about 75° C., from about 50° C. to about 70° C., from about 50° C. to about 65° C., and desirably from about 50° C. to about 60° C., or most desirably from about 50° C. to about 55° C. In one exemplary mode of practice, the liquid composition including polypeptide nuclei and the amphiphilic reagent are individually heated to a temperature of about 50° C.

The liquid composition including polypeptide nuclei and the amphiphilic reagent can be mixed at the elevated temperature to thoroughly combine the reagents, and then heat is allowed to dissipate from the mixture. In many modes of practice, the mixing is performed with sufficient agitation and in a manner to keep the amphiphilic reagent well mixed with polypeptide nuclei. Desirably, mixing is performed to quickly and incrementally increase the concentration of the amphiphilic reagent in the liquid composition of polypeptide nuclei.

The mode of agitation can be chosen based on the factors such as the size of the receptacle containing the amphiphilic agent and the nucleated polypeptide. Such agitation can be performed using vortexing equipment, through use of stirring equipment such as stir bars, or even by manually shaking the receptacle. Mixing is generally carried out until the amphiphilic compound and the nucleated polypeptide are sufficiently combined, which may only take a few seconds, or may be longer for larger volumes.

During and after mixing, free polypeptide is further coalesced around polypeptide nuclei for microparticle formation. The polypeptide is further coalesced by the principle of water exclusion. The phase separation reagent sequesters the water molecules and drives the polypeptide to coalesce around polypeptide nuclei.

As stated, during and after mixing, heat dissipates from the mixture. Following mixing, the polypeptide microparticles can be subjected to a step of cooling. In the cooling step the agitated mixture is brought down to a temperature, eventually, that solidifies the mixture by freezing (such as below 0° C.). The microparticle preparation is kept at this low temperature until completely frozen. During the cooling process, and prior to freezing, there may be further aggregation of the free polypeptide around polypeptide nuclei. Beneficially, the present invention shows that sets of polypeptide microparticles can be formed having desired discrete sizes, those of about 10 μm or less, such as in the range of about 1 μm to about 10 μm.

As a general matter, a rapid cooling step to a low temperature results in the formation of polypeptide microparticles having a smaller microparticle size, such as less than about 3 μm or 4 μm, and more particularly in the range of about 1 μm to about 4 μm, or about 2 μm to about 3 μm. A slower cooling to the low temperature results in a particle size of about 4 μm or greater, such as in the range of 4 μm to about 8 μm, or more specifically in the range of about 5 μm to about 6 μm.

For example, in some modes of practice, a rapid, very low-temperature cooling step is performed. In this step, the microparticles are quickly transferred from the mixing step (such as mixing by vortexing briefly at about 50° C.) to a very low temperature, such as about −40° C. or below, −50° C. or below, −60° C. or below, −70° C. or below, or −80° C. or below. In one exemplary mode of practice, the liquid composition containing the forming microparticles is quickly transferred to a dry ice bath, resulting in microparticles having an average diameter in the range of about 1 μm to about 2 μM, and a very low degree of monodispersity value.

As another example, the liquid composition containing the forming microparticles are quickly transferred from the mixing step to a low temperature, such as in the range of below 0° C. to about 40° C. In one exemplary mode of practice, the liquid composition containing the forming microparticles is quickly transferred to −20° C., resulting in microparticles having an average diameter in the range of about 2 μm to about 3 μm.

As another example, the liquid composition containing the forming microparticles is gradually transferred from the mixing step to a low temperature, such as in the range of below 0° C. to about −40° C. The gradual transfer may include one or more decremental sub-steps of incubating the liquid composition at temperature between the mixing temperature and the low temperature. For example, the liquid composition can be transferred from a mixing temperature of about 50° C. to one or more temperatures below 50° C., and preferably below room temperature 25° C.), but above 0° C. for one or more periods of time, and then finally to a temperature in the range of below 0° C. to about −40° C. The gradual transfer can be carried out over a time period in the range of minutes to hours.

For example, in one mode of practice, the liquid composition containing the forming microparticles are transferred from the mixing step to room temperature (~25° C.) for 30 minutes, then to 4° C. for 30 minutes, and subsequently to −20° C. until frozen. The cooling step can also be performed more gradually, where the temperature is reduced continuously over the cooling period. The process of cooling can be performed manually, or, for example, using commercially available thermocycling machines.

The microparticles can be kept frozen before the microparticles are further processed to remove the phase separation agent. Prior to removal of the phase separation agent, the microparticle preparation is treated to remove the water content in the preparation. The treatment can be a drying step, which can be carried out by a process such as lyophilization.

The lyophilized microparticle preparation can then be subjected to removal of the phase separation agent. In one mode of practice, the dried microparticle preparation is treated (for example, by washing) with an organic solvent, such as chloroform or dichloromethane, to remove the phase separation agent. Repeated washes of the dried lyophilized microparticle preparation can be performed to remove predominantly all of the phase separation agent from the microparticle preparation. The washing steps can be carried out at room temperature.

Following washes, the microparticles can be stored in dried form, and for example, frozen until prepared for use.

As a general matter the method of the invention provides microparticles formed of polypeptide, wherein the amount of nucleating agent is at a higher concentration in the center of the microparticle (i.e., the nucleus), than it is in the portion of the microparticle outside of the nucleus. Some amounts (e.g., trace amounts) or practically no amount of nucleating agent may be present in the portion outside of the nucleus in the formed microparticle.

The polypeptide microparticles produced according to the methods of the invention may have a diameter (mean) from about 100 nm to about 25 μm, more specifically from about 500 nm to about 15 μm, even more specifically from about 0.3 μm to about 10 μm (when observed as individual, discrete microparticles). In particular, the present process provides a set of well-formed high content polypeptide microparticles having an diameter (mean) in the range of about 0.3 μm to about 10 μm, and having a very low degree of monodispersity value.

In many aspects, the method of the invention produces polypeptide microparticles that are spherical or substantially spherical in shape. A spherical polypeptide microparticle will have, from a center of the polypeptide microparticle, the distance from the center to the outer surface of the microparticle is about the same for any point on the surface of the microparticle. A substantially spherical microparticle is where there may be a difference in radii, but the difference between the smallest radii and the largest radii is generally not greater than about 40% of the smaller radii, and more typically less than about 30%, or less than 20%.

The process of the present invention can be used to provide a polypeptide microparticle set having a low size polydispersity (numerically described herein as a low degree of monodispersity value). A low size dispersity means that there is little variation in the size of the microparticles in the set (as compared to a high size dispersity, which means that there is considerable variation in the size of the microparticles of the set). In many aspects, the (set of) microparticles of the invention have a low size polydispersity.

Analysis of particle size distribution can be performed using laser light scattering equipment such as Malvern System 4700, (for particles from 1 nm to 3 μm) or Horiba LA-930 (e.g., for particles from 100 nm to 2 mm). The output from such particle analyzers can provide information on the sizes of individual microparticles of the microparticle set, and the overall amount of microparticles of these sizes showing the distribution of microparticles in terms of size. Analysis providing data on the size distribution can be provided in the form of a histogram, graphically representing the size and size distribution of all the polypeptide microparticles in the set.

The method of the invention can provide a single mode microparticle preparation. In a single mode microparticle preparation, there will be a mean size of microparticles, which is determined, by the particle size (diameter) for each microparticle in the set, divided by the total number of the microparticles in the set. The set will also have a size range, with the lower end of the range referring to the smallest microparticles of the set, and the upper end of the range referring to the largest microparticles of the set. The median size of the set (as compared to the mean, also referred to as the "mode" or "$x_{50}$") is the middle of the range.

Figure 5:
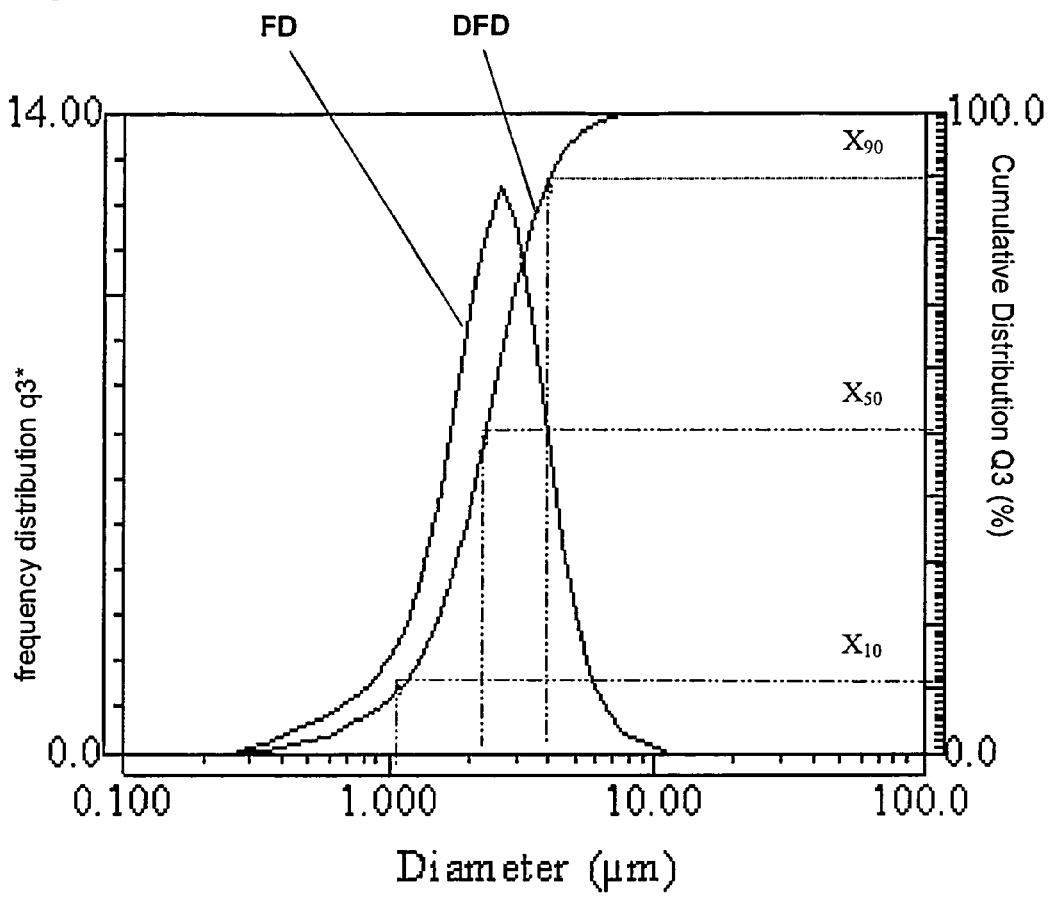
FIG. 5 is an exemplary size dispersity histogram showing a frequency distribution curve and the derivative of the curve representing the cumulative distribution of microparticles in the set.

In some cases, referring to FIG. 5, the size dispersity of microparticle set is graphically represented in the form of a frequency distribution curve (line FD). From this curve, which is usually Gaussian shaped (e.g, "bell shaped"), one can correlate a specific particle size (x axis) with the frequency (y axis on the left hand side of the graph) that particles of this size are encountered in the set. The derivative of this curve (shown in FIG. 5 as line DFD) represents the cumulative distribution of the microparticles in the set. The cumulative distribution curve plots the particle size against the fraction of the total amount of particles that are smaller than, or equal to, the given particle size (y axis on the right hand side of the graph).

In some cases, the particle size distribution of the microparticle set can be described by $x_{10}$, $x_{50}$ and $x_{90}$ values, which are defined as the particle sizes calculated from the cumulative distribution curve at 10%, 50%, and 90% fractions of the total amount of particles, respectively. For example, the particle size where 10% of the total amount of particles are smaller than or equal to that size is defined as the $x_{10}$. In some cases, the microparticle set can be defined by the "degree of monodispersity" (DM) and determined by the following equation:

$$DM=(x_{90}-x_{10})/x_{50}$$

A set of microparticles is more homodisperse as the value of DM approaches 0.

The average size of microparticles in the microparticle set can be calculated knowing the mean size d of the microparticles in the microparticle set. The mean size of the microparticles in the microparticle set is calculated by summation of all products between number of microparticles $n_i$ with size $d_i$ over all sizes i (area under the frequency distribution curve) and dividing that by the total number of particles $\Sigma_i n_i$:

$$d = \frac{\sum_i n_i d_i}{\sum_i n_i}$$

The mode is defined as the particle size at the maximum of the frequency distribution curve.

For example, for a microparticle preparation (i.e., a microparticle set) that has a mean size of 2.5 μm (diameter), and (as derived from the frequency distribution curve of the set), a size at $x_{50}$ of 2.3 μm, a size at $x_{10}$ of 1.1 μm, and a size at $x_{90}$ of 4.0 μm, has a degree of monodispersity of 1.3. (the size difference within 80% of the particles ($x_{90}$-$x_{10}$) divided by the particle size at $x_{50}$, which is 1.3).

According to the methods of the present invention, a microparticle set with a low degree of monodispersity can be prepared.

In some aspects, the degree of monodispersity of the microparticle set is about 5 or less, such as in the range of about 0.5 to about 5, about 4 or less, such as in the range of about 0.5 to about 4, about 3 or less, such as in the range of about 0.5 to about 3, about 2.5 or less, such as in the range of about 0.5 to about 2.5, about 2 or less, such as in the range of about 0.5 to about 2, about 1.5 or less, such as in the range of about 0.5 to about 1.5, about 1.3 or less, such as in the range of about 0.5 to about 1.3, about 1 or less, such as in the range of about 0.5 to about 1, about 0.8 or less, such as in the range of about 0.5 to about 0.8.

In some cases, the microparticle set has a degree of monodispersity as described above, and microparticles of the set have a mean size in the range of about 0.3 μm to about 10 μm (diameter), or a mean size in the range of about 0.5 μm to about 10 μm (diameter).

For example, using the methods of the present invention, a polypeptide microparticle set was prepared having a mean size of about 5.9 μm and the value at $x_{50}$ was about 5.1 μm. Accordingly, the degree of monodispersity was about 1.5.

As another example, using the methods of the present invention, a polypeptide microparticle set was prepared having a mean size of about 2.5 μm and the value at $x_{50}$ was about 2.3 μm. Accordingly, the degree of monodispersity was about 1.3.

As another example, using the methods of the present invention, a polypeptide microparticle set was prepared having a mean size of about 2.8 μm and the value at $x_{50}$ was about 2.7 μm. Accordingly, the degree of monodispersity was about 0.8.

Size polydispersity can also be described in terms of a dispersity index, which is derived from an equation taking into account the size and distribution of microparticles within the microparticle set.

Size polydispersity "D" is defined by the weight average diameter (dw) of the set of polypeptide microparticles divided by the number average diameter (dn) of the set of polypeptide microparticles (dw/dn)

The following definitions and equation is useful for determining size polydispersity.

$n_i$=the number of particle with diameter $d_i$
$d_i$=a particular diameter $$d_n \text{ (number average)} = \text{sum } n_i \times d_i / \text{sum } n_i$$

$$d_w \text{ (weight average)} = \text{sum } n_i \times d_i^2 / \text{sum } n_i \times d_i$$

The polypeptide microparticles of the present invention can be delivered to a site within the body for the therapeutic treatment of a medical condition. Generally, the polypeptide microparticles dissolve when placed in contact with a body fluid, and release polypeptide, which can provide a bioactive effect locally or systemically in the body.

In some aspects the polypeptide microparticles are associated with a system that controls the release of the polypeptide from the microparticles in some manner. Since, in many aspects, the polypeptide microparticles are prepared to dissolve and release polypeptide in an aqueous environment. The polypeptide microparticles can be provided with a coating or can be encapsulated to prevent premature release if the composition is formulated in an aqueous solution. The coating or matrix may also delay the release of the polypeptide from the microparticle after the microparticles have been placed within a patient. The polypeptide microparticles, in conjunction with a polymeric matrix, can provide a particularly effective mechanism for the sustained delivery of polypeptide to a subject.

In some aspects, the polypeptide microparticles are held within a polymeric matrix that is placed or formed at a target location in the body. The polymeric matrix can be in the form of an in-situ formed polymeric matrix, or an implant. Exemplary implants that can include microparticles are described in commonly assigned U.S. Provisional Patent Application No. 60/848,563, filed Sep. 29, 2006 (Varner et al.) which describes biodegradable polysaccharide-based implants which can be placed at a target location in the eye for the treatment of an ocular condition.

The polymeric matrix can also be associated with an implantable medical device, such as in the form of a coating on a surface of the device or a matrix within the device.

The polymeric matrix can be biostable, biodegradable, or can have both biostable and biodegradable properties. The polymeric matrix can be formed from synthetic or natural polymers.

The matrix can be composed of polymeric material (one or more polymers) that allows immobilization of the microparticles. The polymeric material can include one or more homopolymers, copolymers, combinations or blends thereof useful for forming the matrix. Hydrophobic polymers, hydrophilic polymers, or polymers having hydrophobic and hydrophilic properties (such as block or segmented copolymers) can be used to form the matrix. In some cases combinations of polymers having different properties can be used to form the matrix. Hydrophobic polymers are those having no appreciable solubility in water.

Generally, a polymeric material is chosen and used in a composition suitable for forming a matrix with intact microparticles. For example, a polymer can be chosen which is soluble in a liquid that does not destroy the microparticles, such as choroform.

Experimental studies associated with the invention show that Fab microspheres prepared according colloidal gold nucleation and PEG phase separation method of the present invention retained 100% activity (measured by total and active ELISA) after exposure to cloroform for 1 month at 4° C. If the Fab microparticles are not in the microparticular structure of the invention, such exposure to organic solvents could alter the structure of the Fab molecule and result in decreased activity. As such, the polypeptide microparticles are particularly suitable for inclusion in compositions that include a solvent suitable for the preparation of a composition that includes on or more polymers having a hydrophobic property.

In some modes of practice the polypeptide microparticles are entrapped in a matrix formed from synthetic polymers. Synthetic polymers can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/ (meth)acrylamide copolymers. Mixtures of homopolymers and/or copolymers can be used.

In some aspects the first polymer is selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/ or methacrylates, respectively).

Examples of poly(alkyl(meth)acrylates) include those with alkyl chain lengths from 2 to 8 carbons, inclusive. Exemplary sizes of poly(alkyl(meth)acrylates) are in the range of about 50 kilodaltons to about 1000 kilodaltons, about 100 kilodaltons to about 1000 kilodaltons, about 150 kilodaltons to about 500 kilodaltons, and about 200 kilodaltons to about 400 kilodaltons. One exemplary poly(alkyl(meth)acrylate is poly(n-butyl methacrylate).

Examples of poly(aromatic(meth)acrylates) include poly(aryl(meth)acrylates), poly(aralkyl(meth)acrylates), poly(alkaryl(meth)acrylates), poly(aryloxyalkyl (meth)acrylates), and poly(alkoxyaryl(meth)acrylates).

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

Some exemplary natural polymers that can be used to form the matrix are low molecular weight starch-derived polymers as described in commonly assigned U.S. Publication No. 2007/0065481, filed Nov. 11, 2005 (Chudzik et al.). These low molecular weight starch-derived polymers, as exemplified by amylose and maltodextrin, comprise reactive groups, such as polymerizable groups, which can be activated to form a biodegradable matrix that includes the polypeptide microparticles.

Other exemplary natural polymers that can be used to form the matrix are low molecular weight starch-derived hydrophobic polymers as described in commonly assigned U.S. patent application Ser. No. 11/724,553 filed on Mar. 15, 2007. (Chudzik et al.). These low molecular weight starch-derived hydrophobic polymers, as exemplified by amylose and maltodextrin, comprise hydrophobic groups and can be used to form hydrophobic matrices that include the polypeptide microparticles.

In other modes of practice a polypeptide microparticle-containing matrix is formed from a synthetic biodegradable polymer. Exemplary synthetic degradable polymers can be selected from the group of polyesters such as poly(lactic acid) (poly(lactide)), poly(glycolic acid) (poly(glycolide)) poly(lactide-co-glycolide), poly(dioxanone); polylactones such as poly(caprolactone) and poly(valerolactone), copolymers such as poly(glycolide-co-polydioxanone), poly(glycolide-co-trimethylene carbonate), and poly(glycolide-co-caprolactone); poly(ether ester) multiblock copolymers such as poly(ethylene glycol) (PEG)/poly(butylene terephthalate) (PBT) block copolymers (see U.S. Pat. No. 5,980,948) and co-polyester consisting glycolide-$\epsilon$-caprolactone segment and a lactide-glycolide segment; poly(3-hydroxybutyrate), poly(3-hydroxyvalerate), poly(tartronic acid), poly($\beta$-malonic acid), poly(propylene fumarate); degradable polyesteramides; degradable polyanhydrides and polyalkeneanhydrides (such as poly(sebacic acid), poly(1,6-bis(carboxyphenoxy)hexane, poly(1,3-bis(carboxyphenoxy)propane); degradable polycarbonates and aliphatic carbonates; degradable polyiminocarbonates; degradable polyarylates; degradable polyorthoesters; degradable polyurethanes; degradable polyphosphazenes; degradable polyhydroxyalkanoates; degradable polyamides; degradable polypeptides; copolymers thereof, and multi-block copolymers as described in EP1555278.

In some embodiments the polypeptide microparticles are present in a polymeric matrix including a first polymer that is hydrophobic and a second polymer that comprises hydrophobic and hydrophilic portions. Specific examples of such first and second polymers are poly(n-butyl methacrylate) and poly(ethylene glycol) (PEG)/poly(butylene terephthalate) (PBT) block copolymer, respectively (see commonly assigned U.S. Pub. No. 2008/0038354; Slager et al.). In some cases the polymeric matrix can include another (third) polymer that is blendable with the first polymer. A specific examples of a third polymer is poly(ethylene-co-vinyl acetate). The third polymer can be present in the matrix along with the first and second polymer, as a coated layer (e.g., a topcoat) on the polymeric matrix, or both.

Imaging agents may also be included in the microparticle or matrix. These agents are capable of imaging a desired site, e.g., tumor, in vivo. Examples of imaging agents include substances having a label that is detectable in vivo, e.g., antibodies attached to fluorescent labels.

The polypeptide microparticles can be associated with a medical device. In some cases, a microparticle-containing coating is formed on the surface of a medical article that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, a matrix of polymeric material with microparticles, such as a coating, is utilized in connection with an ophthalmic article. The ophthalmic article can be configured for placement at an external or internal site of the eye. In some aspects, the articles can be utilized to deliver a hydrophilic bioactive agent to an anterior segment of the eye (in front of the lens), and/or a posterior segment of the eye (behind the lens). Suitable ophthalmic devices can also be utilized to provide bioactive agent to tissues in proximity to the eye, when desired. Compositions including polymeric material and microparticles can be used either for the formation of a coating on the surface of an ophthalmic article, or in the construction of an ophthalmic article.

Articles configured for placement at an internal site of the eye can reside within any desired area of the eye. In some aspects, the ophthalmic article can be configured for placement at an intraocular site, such as the vitreous. Illustrative intraocular devices include, but are not limited to, those described in U.S. Pat. No. 6,719,750 B2, which describes a non-linear intraocular device.

Therapeutic liquid delivery compositions can be prepared that include the polypeptide microparticles. The liquid composition can be prepared for the delivery of the polypeptide microparticles via injection into a target location in the body. For example, the microparticle compositions can be formulated for subcutaneous, intramuscular, and intravenous injections, intrathecal, intraperitoneal, or intraocular injections. If the microparticles do not include a coating or are not encapsulated, the composition is preferably prepared with the microparticles in a non-aqueous composition.

Polypeptides that are released from the microparticles can be used to treat specific diseases. The polypeptide can be used to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

In some cases the polypeptides of the invention are antibodies or antibody fragments that are used to treat disease, such as those described herein.

A polypeptide can be used to treat or detect hyperproliferative disorders, including neoplasms. A polypeptide released from the microparticles of the present invention may inhibit the proliferation of the disorder through direct or indirect interactions. Alternatively, a polypeptide may cause proliferation of cells, which can inhibit a hyperproliferative disorder. For example, the polypeptide can promote an immune response by causing the proliferation, differentiation, or mobilization of T-cells. This immune response may be increased by either enhancing an existing immune response, or by initiating a new immune response.

Examples of hyperproliferative disorders that can be treated include, but are not limited to neoplasms located in the bone, urogenical tissue, digestive system, liver, pancreas, endocrine glands, eye, nervous system, lymphatic system, spleen, and mammary tissue.

A polypeptide released from the microparticles of the present invention may be used to treat infectious disease. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide may directly inhibit the infectious agent, without necessarily eliciting an immune response.

A polypeptide can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocartritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs with limited or no scarring. Regeneration also may include angiogenesis.

A polypeptide may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polypeptide may also increase or decrease the differentiation or proliferation of embryonic stem cells.

A polypeptide may be used to modulate mammalian metabolism affecting catabolism, anabolism, processing, utilization, and storage of energy.

In some aspects of the invention, the microparticles are used to treat an ocular disease. The polypeptide microparticles can be used in ocular implants or in association with an implantable ocular device to treat indications such as angiogenesis, inflammation, and degeneration.

For example, the polypeptide microparticles can be used for the treatment of diabetic retinopathy, which is characterized by angiogenesis in the retinal tissue. Diabetic retinopathy has four stages. While the implant can be delivered to a subject diagnosed with diabetic retinopathy during any of these four stages, it is common to treat the condition at a later stage. The polypeptide can be an anti-angiogenic factors used to treat the angiogenesis.

The treatment of diabetic retinopathy can be accomplished by placing the polypeptide microparticles (such as carried by an implant or ocular implantable device) at target location so that anti-angiogenic polypeptide is released and affect the sub-retinal tissue.

EXAMPLE 1

$CaCl_2$-Nucleated Fab Microparticles

Non-specific rabbit Fab (Southern Biotech) was desalted using a BioRad desalting column (Econo-Pac 10 DG) and then re-concentrated to 15.0 mg/mL in 5 mM sodium phosphate buffer, pH 7.4. Cold solutions of Fab and $CaCl_2$ were combined and then put back at 4° C. In a microcentrifuge tube, 1 µl from a stock solution of 500 mM $CaCl_2$, was added to 200 µl of 15 mg/ml rabbit Fab at pH 7.4 for a final $CaCl_2$ concentration of 2.5 mM. The solution was incubated stationary at 2-8° C. for one hour. A very slight cloudiness was observed indicating formation of polypeptide nuclei. The nucleated Fab/$CaCl_2$ solution was immediately transferred to a 50° C. incubator for 15 minutes.

Figure 1B:
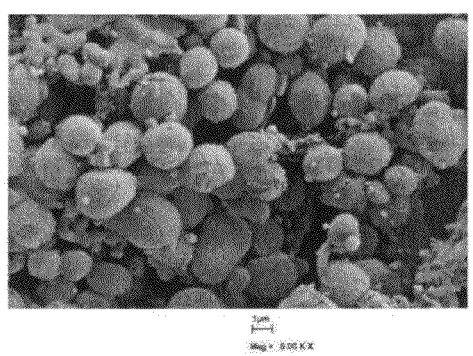

A solution of 30%, 20,000 MW PEG was heated to 50° C. and 65 µl was added slowly and drop wise to the protein solution while vortexing at a moderate speed over a period of tens of seconds. After addition of PEG, the mix was placed into a −20° C. freezer for three hours followed by overnight lyophilization on a benchtop lyophilizer with the samples kept at room temperature and the trap cooled to approximately −50° C. On the following day, the remaining cake was washed four times with excess chloroform using first a separatory funnel followed by a 0.2 µm Spinfilter, Amicon UltrafreeCl at 2300×g for 15 minutes. Particle analysis was performed using scanning electron microscopy, and the images are shown as FIGS. 1a and 1b.

EXAMPLE 2

Colloidal Gold-Nucleated Fab Microparticles

A 5 mM phosphate buffer was prepared by diluting 25 mL of a 10× phosphate stock solution (10×PBS without NaCl) in DI water (18.1 Ω) to a total volume of 500 mL. pH was adjusted to pH=7.31 after adding one drop of concentrated $H_3PO_4$ solution.

Fab (rabbit anti-goat (RαG)) was desalted using a BioRad desalting column (Econo-Pac 10 DG). Storage buffer from the columns were disposed and the columns were equilibrated with 20 mL of 5 mM PBS. 2.5 ml of Fab ($A_{280}$ (50 μL)=0.953; ε=1.53=>14.1 mg/mL) was put on each column and completely absorbed. Fab was eluted from the columns with 4 mL of 5 mM PBS. The Fab was concentrated using 4 centrifuge filters (10 kDa cutoff, PALL Lifesciences), which were filled with 4 mL of the desalted Fab eluate and spun at 5500 g for 50 minutes at 10° C. The concentrated Fab supernatants were combined providing Fab at a concentration of 20.4 mg/mL as determined spectrophotometrically (@$A_{280}$). The pH of the protein solution was adjusted to 5.3 by adding 10 ul of 3N HCl solution.

At room temperature, 5 nm colloidal gold (MP Biomedicals (Solon, Ohio) Cat #IC15401005) in a volume of 5 μL was added to 200 μL Fab 20 mg/ml in 5 mM NaCl-free PBS (pH=5.3) and incubated at 50° C. for 30 minutes.

A PEG solution (20 kDa PEG dissolved to 30% w/v in water, pH=5) was warmed to 50° C., and 70 μL of the PEG solution was added dropwise to the colloidal gold-nucleated Fab solution while vortexing for several seconds.

The PEG/colloidal gold-nucleated Fab mixture was then cooled. Three different cooling conditions were individually performed. In one condition, the PEG/colloidal gold-nucleated Fab mixture was put on dry ice. In another condition, the PEG/colloidal gold-nucleated Fab mixture was put at −20° C. In another condition, the PEG/colloidal gold-nucleated Fab mixture was put first at room temperature (~25° C.) for 30 minutes, then at 4° C. for 30 minutes, and subsequently at −20° C. until frozen.

The frozen mixtures were then lyophilized as described in Example 1, and PEG was extracted using chloroform. For chloroform extraction, 1 mL of chloroform was added to the microtube with lyophilized Fab microparticles and the Fab particles creamed on the surface of the solution. The particles were aspirated with a glass pipette and mixed in 1 mL of fresh chloroform. The extraction/aspiration was repeated three times. A sample of the Fab microparticles in chloroform was dried on a microscope glass slide and analyzed using a microscope with a digital camera at 500×.

Figure 2A:
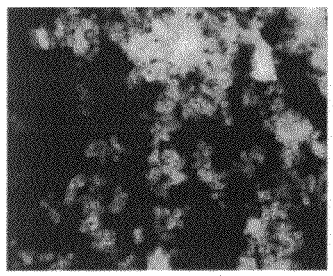
FIGS. 2a-2c are SEM images of colloidal gold-nucleated Fab microparticles.
Figure 2B:
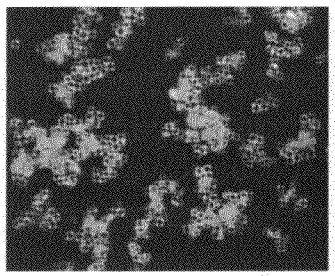
Figure 2C:
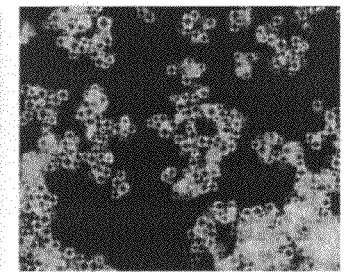

Imaging revealed that the particular Fab microparticles sizes could be obtained depending on the cooling conditions. For particles cooled immediately on dry ice, the average size of the microparticles was in the range of 1-2 microns (FIG. 2a). For particles cooled immediately at −20° C., the average size of the microparticles was in the range of 3-4 microns (FIG. 2b). For particles cooled immediately at room temp, then at 4° C. and subsequently at −20° C., the average size of the microparticles was in the range of 5-6 microns (FIG. 2c).

EXAMPLE 3

Colloidal Gold-Nucleated Fab Microparticles

Colloidal gold-nucleated Fab microparticles having an average diameter in the range of 2-3 microns were prepared in a scaled up procedure.

RαG Fab was desalted and concentrated according to the procedure described in Example 2. To 2 ml Fab solution (40 mg) 50 uL of colloidal gold was added (5 nm, 0.01% w/v, 5 μg gold, 0.00013% w/w protein) solution was added.

Figure 3:
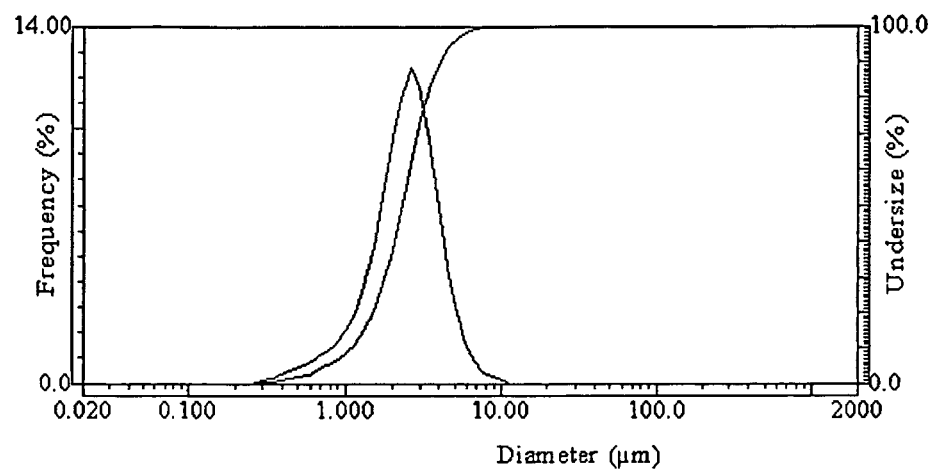
FIG. 3 is a size dispersity histogram generated by laser light scattering analysis of colloidal gold-nucleated Fab microparticles having a mean particle size in the range of 2-3 microns.

The Fab/colloidal gold solution was put at 50° C. for 40 minutes in a 15 ml centrifuge tube. A 30% w/v PEG 20 kDa solution was prepared in DI water, the pH adjusted to 5, and then warmed to 50° C. A hole was drilled in the screw-cap and 700 μL of the PEG solution (5.25× protein weight), was dropped into the Fab/colloidal gold solution through the hole in the cap while vortexing. A slightly turbid solution was obtained, which was then poured into a plastic Petri-dish. The dish was covered and put at −20° C. for 1.5 hour, and then on dry ice for 30 minutes. The initially glossy appearance of the PEG/Fab/colloidal gold suspension became matt and solid. The frozen suspension was lyophilized in a vacuum oven at room temperature over night. SEM showed particles with average size of in the range of 2-3 micron and having a low size polydispersity. Samples were analyzed using a Horiba LA-930 laser light scattering particle analyzer to measure particle size and distribution. The histogram of the size dispersity is shown in FIG. 3.

EXAMPLE 4

Colloidal Gold-Nucleated Fab Microparticles

Colloidal gold-nucleated Fab microparticles having an average diameter in the range of 5-6 microns were prepared in a scaled up procedure.

Preparation of RαG Fab, nucleation of the Fab particles using colloidal gold, and phase separation using PEG was performed as described in Example 3.

Following addition of the PEG solution to the colloidal-gold nucleated Fab and placement into a plastic Petri-dish, the mixture was left at room temperature for 30 minutes, then put at 4° C. for 30 minutes and then placed at −20° C. until completely frozen. The batch was lyophilized and PEG was extracted using chloroform.

Figure 4:
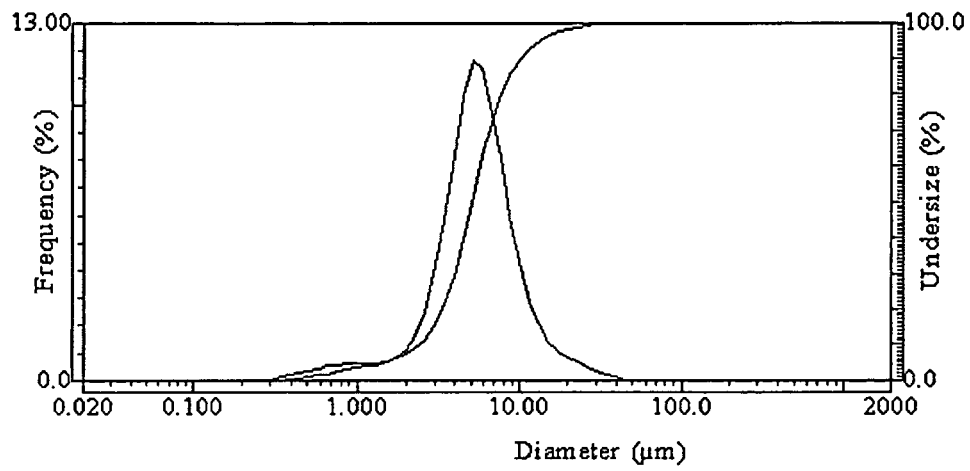
FIG. 4 is a size dispersity histogram generated by laser light scattering analysis of colloidal gold-nucleated Fab microparticles having a mean particle size in the range of 5-6 microns.

SEM showed particles with average size of in the range of 5-6 microns and having a low size polydispersity. Samples were analyzed using a Horiba LA-930 laser light scattering particle analyzer to measure particle size and distribution. Details of the analysis are shown in FIG. 4.

EXAMPLE 5

Polyplex-Nucleated Fab Microparticles

Polyethyleneimine (PEI, Sigma, 25 kDa branched) was dissolved at 9 mg in 10 mL distilled deionized water (DDW). Using HCl the initial basic pH was brought back to 7.4 and total volume was adjusted with DDW to 20 mL (creating 10 mM primary amino groups or "N"). Herring DNA 600-1000 bp (Lofstrand, Gaithersburg, Md.) was dissolved in DDW at 1 μg/μL. One μg of DNA contains 3 nmol of negatively charged phosphate groups ("P"). DNA was mixed with PEI to provide DNA/PEI solutions with N/P ratios of 12 and 24, individually.

For a N/P ratio of 12, 5.5 µg DNA (5.5 µL) was mixed with 13.8 µL sucrose 0.75 M (2.57 g in 10 ml water, 25% w/v) to yield a 150 mM or 5% w/v solution. The PEI solution in an amount of 20 µL was mixed with 4 µL of the 0.75 M sucrose solution. The PEI mixture was dropped slowly into the DNA solution. After addition the mixture was vortexed briefly.

For a N/P ratio 24:2.75 µg DNA (2.75 µL) was mixed with 0.7 µL sucrose 0.75 M (2.57 g in 10 ml water, 25% w/v) to yield a 150 mM or 5% w/v solution. The PEI solution in an amount of 20 µL was mixed with 4 µL 0.75 M sucrose solution. The PEI mixture was dropped slowly into the DNA solution. After addition the mixture was vortexed briefly.

A Fab solution, in an amount of 200 µL and at a concentration of 20 mg/mL at pH 7.4 was added to the DNA/PEI polyplex solutions individually at room temperature and the samples were put in an oven at 50° C. for 20 minutes. After this, 70 µL of a PEG 20 kDa solution 30% w/v (warmed to 50° C.) was added dropwise to the polyplex/protein mixture while vortexing several seconds.

The samples were either put back immediately in the oven for 30 minutes at 50° C. or left out of the oven and put at room temperature for 30 minutes. Subsequently the mixtures were put in the freezer at −20° C. until frozen and lyophilized. The PEG was extracted with chloroform as described above. A sample was put on a microscope glass slide for SEM analysis.

EXAMPLE 6

Non-Nucleated Fab Particles

The preparation of Fab particles without the use of a nucleating agent was attempted.

A non-specific rabbit Fab was prepared according to Example 2. A solution of 30%, 20,000 MW PEG was heated to 50° C. and 130 µl was added slowly and drop wise to the protein solution while vortexing at a moderate speed over a period of tens of seconds.

The remainder of the process was carried out according to Example 1.

The process performed without the nucleation agent resulted in amorphous particles, with particles>5 um that were not well shaped and with cracks.

EXAMPLE 7

Colloidal Gold-Nucleated Fab Microparticles

The preparation of Fab particles was performed with the use of a nucleating agent and mixing the phase separation agent at various temperatures.

The process according to Example 2 was performed with the exception that three different temperatures (20° C., 37° C., and 50° C.) were used when the PEG was added to the gold-nucleated Fab solution.

Raising the temperature above room temperature resulted in lower dispersity for the microparticle sets, with the best results seen at 50° C.

What is claimed is:

1. A polypeptide microparticle comprising an antibody or an antibody fragment polypeptide and a nucleus or nuclei, the nucleus or nuclei comprising a nucleating agent, wherein the polypeptide is present in an amount of 90% or greater in the polypeptide microparticle by weight, and wherein the polypeptide microparticle has a substantially spherical shape and a diameter in the range of 0.3 µm to 10 µm, and having a weight ratio of nucleating agent to polypeptide in the range of about 1:100 to 1:10,000, respectively.

2. The microparticle of claim 1 wherein the nucleating agent is selected from the group consisting of divalent cations, noble metal colloids, nucleic acid polyplexes, and thermoplastic nanospheres.

3. The microparticle of claim 2 wherein the nucleating agent comprises a colloidal gold.

4. The microparticle of claim 2 wherein the nucleating agent comprises a nucleic acid polyplex.

5. The microparticle of claim 2 wherein the nucleating agent comprises a divalent cation.

6. The microparticle of claim 1 wherein the polypeptide comprises a Fab or Fab'2 fragment.

7. The microparticle of claim 1 wherein the polypeptide has a molecular weight in the range of 10,000 Da to 200,000 Da.

8. The microparticle of claim 1 wherein the polypeptide is present in an amount of 99% or greater of the weight of the microparticle.

9. The microparticle of claim 1 having a diameter in the range of 1 µm to 4 µm.

10. A microparticle set comprising a plurality of polypeptide microparticles comprising an antibody or an antibody fragment polypeptide, wherein polypeptide is present in an amount of 90% or greater in the polypeptide microparticles of the set and individual polypeptide microparticles in the set comprise a nucleus or nuclei comprising a nucleating agent, wherein the microparticles have a weight ratio of nucleating agent to polypeptide in the range of about 1:100 to 1:10,000, respectively, and wherein the set has a degree of monodispersity of 5 or less.

11. The microparticle set of claim 10 wherein the set has a degree of monodispersity in the range of 0.5 to 5.

12. The microparticle set of claim 10 wherein the microparticles of the set have a mean diameter in the range of about 0.3 µm to about 10 µm.

13. A polypeptide microparticle formed according to a method comprising steps of
coalescing antibody or an antibody fragment polypeptides with a nucleating agent to form polypeptide nuclei, wherein coalescing is performed in solution;
mixing a phase separation reagent with the solution to further coalesce polypeptide around the nuclei;
cooling the mixture; and
removing all or a portion of the phase separation reagent from the mixture, where, in the polypeptide microparticles that are formed, polypeptide is present in an amount of 90% or greater of the weight of the microparticle and wherein the nucleating agent and polypeptide are present in the microparticles at weight ratio in the range of about 1:100 to 1:10,000, respectively.

14. A therapeutic composition comprising polypeptide microparticles and configured for administration to a subject, wherein the polypeptide microparticles comprise an antibody or an antibody fragment polypeptide
and a nucleus or nuclei, the nucleus or nuclei comprising a nucleating agent, wherein the polypeptide is present in an amount of 90% or greater in the polypeptide microparticle by weight, wherein the microparticles have a weight ratio of nucleating agent to polypeptide in the range of about 1:100 to 1:10,000, respectively, wherein the polypeptide microparticle has a substantially spherical shape and a diameter in the range of 0.3 µm to 10 µm, and wherein the polypeptides can be released from the microparticles and provide a therapeutic effect following administration to the subject.

15. The therapeutic composition of claim 14 configured for subcutaneous, intramuscular, intravenous, intrathecal, intraperitoneal, or intraocular injection.

16. The therapeutic composition of claim 14 which comprises a non-aqueous liquid.

17. The therapeutic composition of claim 14 wherein the nucleating agent comprises a colloidal gold.

18. The therapeutic composition of claim 14 wherein the polypeptide microparticle have a diameter in the range of 1 μm to 4 μm.

* * * * *